(12) United States Patent  
Stuba et al.

(10) Patent No.: US 7,977,658 B2  
(45) Date of Patent: Jul. 12, 2011

(54) FLEXIBLE INFRARED DELIVERY APPARATUS AND METHOD

(75) Inventors: Robert M. Stuba, Macedonia, OH (US); Michael S. Epstein, Annapolis, MD (US); Richard M. Wolf, Hudson, OH (US)

(73) Assignee: Precision Endoscopic Technologies, Annapolis, MD (US)

( * ) Notice: Subject to any disclaimer, the term of this patent is extended or adjusted under 35 U.S.C. 154(b) by 49 days.

(21) Appl. No.: 12/137,691

(22) Filed: Jun. 12, 2008

(65) Prior Publication Data

US 2008/0308753 A1  Dec. 18, 2008

Related U.S. Application Data

(60) Provisional application No. 60/929,164, filed on Jun. 15, 2007.

(51) Int. Cl.  
*A61B 18/18* (2006.01)  
*A61N 5/06* (2006.01)

(52) U.S. Cl. .......... 250/504 H; 606/15; 606/16; 606/17; 607/88; 607/90; 607/93

(58) Field of Classification Search ............ 250/504 H, 250/504 R; 606/15, 16, 17; 607/88, 90, 607/93

See application file for complete search history.

(56) References Cited

U.S. PATENT DOCUMENTS

| 3,348,547 | A |  | 10/1967 | Kavanagh |
| 4,211,229 | A |  | 7/1980 | Wurster |
| 4,233,493 | A |  | 11/1980 | Nath |
| 4,266,548 | A |  | 5/1981 | Davi |
| 4,539,987 | A | * | 9/1985 | Nath et al. ................ 606/3 |
| 4,572,189 | A |  | 2/1986 | Smith et al. |
| 4,589,404 | A |  | 5/1986 | Barath et al. |
| 4,860,172 | A | * | 8/1989 | Schlager et al. ............. 362/553 |

(Continued)

FOREIGN PATENT DOCUMENTS

EP    0 752 254 A1    1/1997

(Continued)

OTHER PUBLICATIONS

Infrared fiber-optic endoscope; NASA Tech Briefs, Oct. 2002; 7 pages.

(Continued)

*Primary Examiner* — Jack I Berman  
(74) *Attorney, Agent, or Firm* — Antonelli, Terry, Stout & Kraus, LLP.

(57) ABSTRACT

A flexible infrared delivery apparatus useful for endoscopic infrared coagulating of human or animal blood and tissue or for other uses employs a source of infrared radiation which is not a laser and an elongated flexible fiber optic member which transmits radiation from the source to a contact portion at a distal end of the member and to a material such as human or animal tissue proximate the contact portion. The elongated member has an outer diameter which enables it to be inserted into and through an accessory channel of an endoscope to view the human or animal tissue or material to be treated with infrared radiation. A connector on the proximal end of the member allows the elongated member to be quickly connected to and disconnected from the apparatus where the member is aligned for receiving infrared radiation from the source. The contact portion defines a size, direction and shape of a radiation delivery area from the member to the human or animal tissue or material proximate the contact portion.

25 Claims, 13 Drawing Sheets

U.S. PATENT DOCUMENTS

| | | | |
|---|---|---|---|
| 5,374,266 | A | 12/1994 | Kataoka et al. |
| 5,519,208 | A | 5/1996 | Esparza et al. |
| 5,591,160 | A * | 1/1997 | Reynard .................. 606/15 |
| 5,993,442 | A | 11/1999 | Omori |
| 6,164,280 | A | 12/2000 | Everett et al. |
| 6,214,033 | B1 | 4/2001 | Ii et al. |
| 6,267,779 | B1 | 7/2001 | Gerdes |
| 6,336,738 | B1 * | 1/2002 | Feuermann et al. .......... 362/583 |
| 6,530,919 | B1 * | 3/2003 | Chodorow et al. ............. 606/13 |
| 6,605,082 | B2 | 8/2003 | Hareyama et al. |
| 6,616,653 | B2 * | 9/2003 | Beyar et al. .................... 606/14 |
| 6,953,458 | B2 | 10/2005 | Loeb |
| 7,359,601 | B2 | 4/2008 | Loeb |
| 7,425,296 | B2 | 9/2008 | Cochran et al. |
| 2004/0254619 | A1 * | 12/2004 | Feuermann et al. ............ 607/88 |
| 2005/0054900 | A1 | 3/2005 | Mawn et al. |
| 2005/0065531 | A1 | 3/2005 | Cohen |
| 2006/0052661 | A1 | 3/2006 | Gannot et al. |
| 2006/0064080 | A1 | 3/2006 | Cao |
| 2006/0129211 | A1 | 6/2006 | Canitano et al. |

FOREIGN PATENT DOCUMENTS

WO      WO 01/78618 A1     10/2001

OTHER PUBLICATIONS

NASA-Inspired Shape-Sensing Fibers Enable Minimally Invasive Surgery; NASA Tech Briefs; (NASA—Developed Roots) Feb. 1, 2008; 3 pages.

NASA-Inspired Shape-Sensing Fibers Enable Minimally Invasive Surgery; NASA Tech Briefs; Feb. 1, 2008; 3 pages.

A Look From Inside; Originating Technology/NASA Contribution; NASA Tech Briefs; Jan. 1, 2004; 4 pages.

Simulating an Arthroscopic Surgical Instrument; Algor, Inc., Pittsburgh, Pennsylvania; NASA Tech Briefs; Feb. 1, 2003; 3 pages.

NASA Tech Briefs Insider Blog; Pill Predictions; Feb. 5, 2008; 6 pages.

Japan Atomic Energy Agency Develops Prototype of Ultra-thin Endoscope for Prenatal Treatment; The Free Library by Farlex; Mar. 8, 2006; 4 pages.

Supplementary European Search Report dated Jun. 8, 2010; Application No. 08768373.6-2305/2166921 PCT/US2008007320.

* cited by examiner

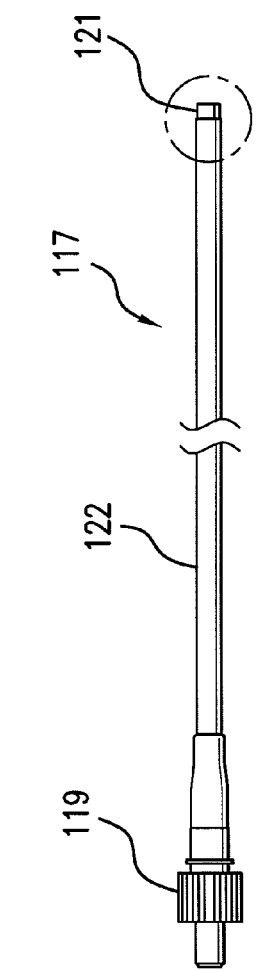
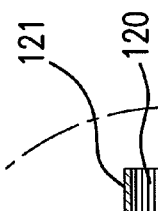
FIG.13
FIG.11
FIG.12
FIG.14

FLEXIBLE INFRARED DELIVERY APPARATUS AND METHOD

RELATED APPLICATION

This application claims priority under 35 U.S.C. §119 of provisional application No. 60/929,164 filed Jun. 15, 2007. The disclosure of the provisional application is incorporated herein by reference.

TECHNICAL FIELD

The present invention relates to a flexible infrared delivery apparatus and method for generating, transmitting, and delivering infrared energy from a source of infrared radiation which is not a laser for efficiently and quickly raising the temperature of a target material such that a desired change, response, or transformation of the material is created. A variety of industrial applications are envisioned for the invention, particularly in situations that may require heat to be quickly delivered to a very specific location that may be a significant distance from a safe and practical heat source, or may be in a location that is very difficult to reach except by a tortuous or highly articulated conduit or path. In a preferred form, an endoscopic infrared coagulation apparatus is provided for use in an accessory channel of an endoscope to coagulate target blood and tissue within a human or animal subject.

BACKGROUND AND SUMMARY

Infrared coagulation or photocoagulation is well known to medical science. It is a technique in which abnormal tissue is exposed to a burst of infrared energy. This heats the tissue locally, causing blood in veins in the tissue to coagulate (harden) and the abnormal tissue to shrink. Photocoagulation is a somewhat less aggressive method of tissue transformation than other known methods such as electrocautery, cryotherapy, laser ablation or argon plasma coagulation.

Infrared coagulation for outpatient treatment of internal first and second degree hemorrhoids and some third degree ones is known. In the known method, high intensity infrared light is transmitted through a rigid quartz probe which is inserted directly into the rectum and infrared energy applied for 1.5 to 2 seconds three to eight times to a localized area of hemorrhoids to coagulate vessels and tether the mucosa to subcutaneous tissues. Generally only one section of the hemorrhoids is treated per visit. Patients generally have three areas that need treatment and so have to return several times at intervals until all have been controlled. Infrared coagulation is quick (10 to 15 minutes a visit), effective, and painless, and patients can return immediately or the next day. Eighty per cent of patients treated by this conventional method are reported to be free of symptoms at three months.

A drawback of existing infrared coagulation treatment is that it is a "blind" procedure, in the sense that the physician has difficulty seeing the area being treated. For this reason, infrared coagulation can be inaccurate, increasing the need for multiple repeat treatments. There is a need for an improved apparatus and method for treatment of hemorrhoids which can be used in conjunction with a flexible colonoscope or sigmoidoscope, providing the physician with direct visualization of the treatment site, and from numerous directions and angles, facilitating pinpoint accuracy of treatment and immediate visual confirmation of the location and extent of treatment. The present invention addresses this need.

The apparatus of the invention for delivering infrared energy to a material comprises a source of infrared radiation which is not a laser, an elongated flexible fiber optic member for transmitting radiation from the source from a proximal end of the member to a distal end of the member and to a material proximate the distal end, and a connector on the proximal end of the elongated member for quickly connecting the member to and disconnecting the member from the apparatus where the member is aligned for receiving infrared radiation from the source. In the preferred embodiment, the apparatus is an endoscopic infrared coagulation apparatus for use in an accessory channel of an endoscope to coagulate targeted tissue within a human or animal subject.

The apparatus is a contact-type apparatus in that the elongated member includes at the distal end of the member a contact portion for contacting the material to be treated, the contact portion defining a size, direction and shape of a radiation delivery area from the member to a material to be treated proximate the contact portion. The use of a multiple wavelength, non-coherent source of infrared radiation, e.g. not a laser, in the contact type apparatus rather than a converging laser beam focused from above the material which must pass through intervening body fluids, for example, in the case of treating internal human tissue, that can possibly disrupt the beam and treatment and cause errors in treating the correct site, allows the safe and efficient transmission and delivery of infrared radiation to a highly specific location. The delivery is through a small-diameter, highly flexible component which can be used in highly articulated positions, such as in a 180 degree bend or in a "retroflexed" position in a flexible endoscope. The apparatus requires no gas for its use and requires intimate contact between the contact portion of the distal end of the elongated flexible fiber optic member and the target tissue in order for significant transfer of infrared energy to occur, making it less likely for inadvertent energy transfer and tissue damage than with a laser, which can irradiate significant energy without being in contact with the tissue.

In the example embodiments, the source of infrared radiation is an infrared lamp which radiates electromagnetic energy primarily in the infrared region, but which includes both visible and infrared radiation for transmission through the elongated member. The elongated member in the example embodiments includes an inner flexible fiber optic body and outer protective sheath, the inner flexible fiber optic body being a multicomponent transparent fiber bundle. The contact portion for contacting the material/tissue includes an exposed, radiation emitting portion of the multicomponent transparent fiber bundle of the fiber optic member. In one form of the invention, the contact portion defines a radiation delivery area with a direction having both radial and axial direction components with respect to a longitudinal axis of the elongated flexible fiber optic member. According to another feature of the invention, the contact portion defines a radiation delivery area wider than a diameter of the distal end of the elongated flexible fiber optic member. In another variation according to the invention, the contact portion defines a radiation delivery area with a direction in only an axial direction with respect to a longitudinal axis of the elongated flexible fiber optic member.

The method and apparatus of the invention allow the transmission and delivery of infrared energy to a highly specific location through a small-diameter flexible component. In the preferred embodiments, the apparatus creates the opportunity for gastroenterologists and physicians and other medical specialists to treat various conditions with infrared energy using a flexible endoscope, which offers direct visualization of the treatment site, pinpoint accuracy of treatment, and immediate visual verification of the status of treatment. The apparatus and method may be used to coagulate human and animal tissue, for treatment of small vascular malformations, removal of tissue, treatment of small tumors or lesions, and hemostasis. The apparatus and method are especially useful for the treatment of hemorrhoids, and possibly other conditions such as angiodysplasia of the colon, gastric antral vascular ectasis (watermelon stomach), esophageal reflux disease, and Barrett's esophagus. The apparatus does not require the passing of electrical current inside the patient's body as in electrocautery and therefore inherently prevents less risk to patients and also has the advantage of being far less expensive than electrocautery devices such as bipolar probes.

These and other features and advantages of the invention will become more apparent when taken in connection with the accompanying drawings and the following detailed description of several embodiments in accordance with the invention.

BRIEF DESCRIPTION OF DRAWINGS

FIG. 11 is an enlarged side view of the elongated flexible fiber optic member of the apparatus of FIGS. 7-10, sectioned with a middle portion thereof not being shown, depicting the proximal end of the member with a connector thereon for quick connection to and disconnection from the apparatus, and showing the distal end of the member for engaging human or animal tissue;

FIG. 12 is a left end view of the member of FIG. 11;

FIG. 13 is a right end view of the member of FIG. 11;

FIG. 14 is an enlarged side view, partially in section, of the distal end portion of the member within the circle in FIG. 11;

DETAILED DESCRIPTION

Figure 1:
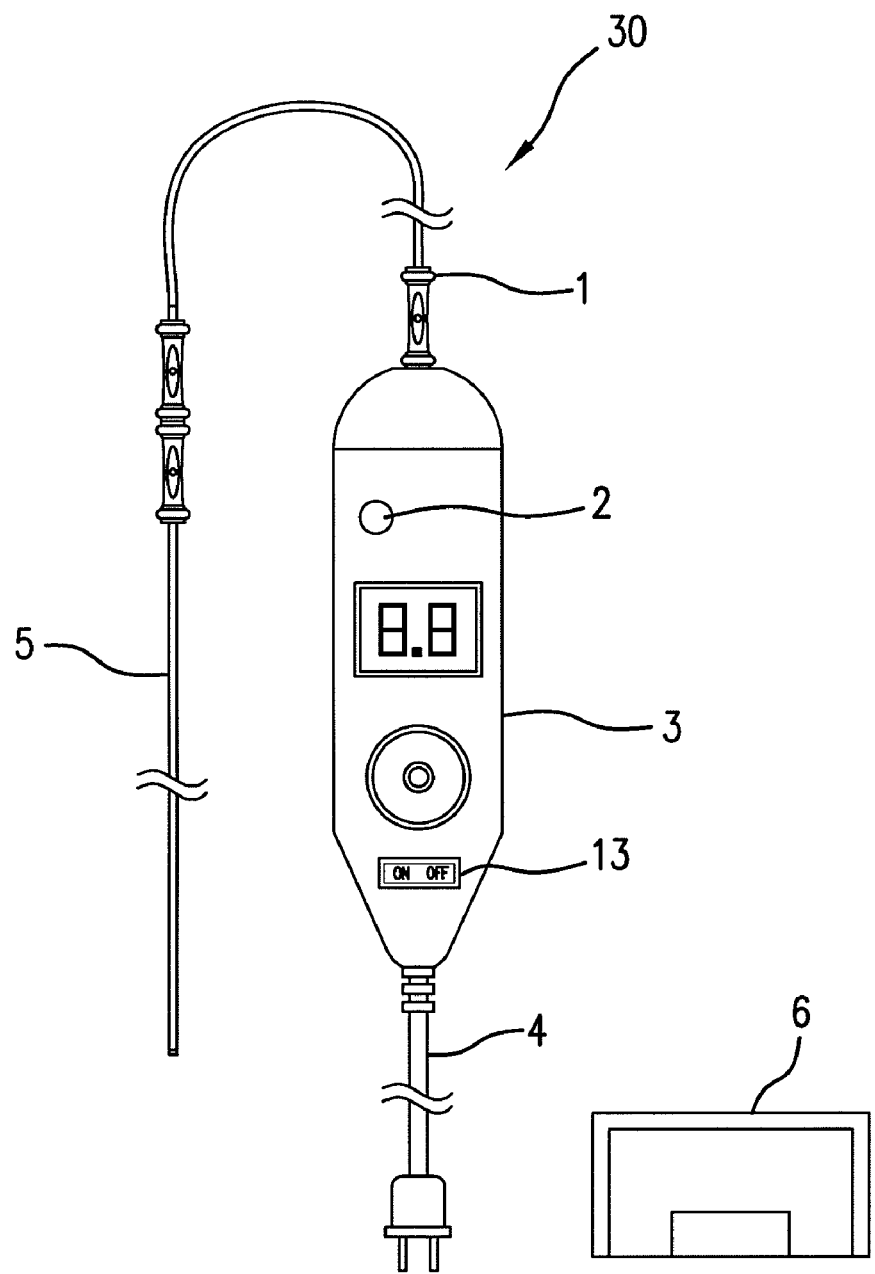
FIG. 1 is a top plan view of a first embodiment of an apparatus of the invention for delivering infrared energy to a material.

Referring now to the drawings, in the example embodiments apparatus 30 in FIGS. 1-6 and apparatus 100 in FIGS. 7-14 are endoscopic infrared coagulation devices, that is, medical devices whose intended use according to the method of the invention is to treat hemorrhoids and other lesions in the gastrointestinal tract through flexible endoscopes such as colonoscopes, sigmoidoscopes, enteroscopes and gastroscopes. The apparatus facilitates coagulation of tissue at specific target sites through the transmission of non-laser infrared energy through a small diameter, elongated flexible fiber optic member which is inserted into and through an accessory channel of the endoscope. Usage of the endoscope infrared coagulation devices 30 and 100 is indicated when a physician, using a colonoscope, sigmoidoscope, gastroscope, or other diagnostic or therapeutic endoscope, has visually identified a hemorrhoid or other tissue within the gastro intestinal system that may require cauterization or coagulation.

The apparatus 30 of FIGS. 1-6 for delivering infrared energy to a material includes a source 8 of infrared radiation which is not a laser. The infrared light source 8 in the example embodiment is a 150 watt tungsten halogen bulb with a gold plated reflector but other sizes and types of non-coherent, multiple wavelength infrared radiation sources could be employed. An elongated flexible fiber optic member 5 according to the invention transmits radiation from the source from a proximal end 31 of the member to a distal end 32 of the member and to a material, e.g. human or animal tissue, proximate the distal end. The elongated member 5 has a small diameter enabling the member to be inserted into and through an accessory channel in an endoscope. The internal diameter of the accessory channel, also referred to as the working channel, in the typical endoscope is 3.7 to 4.2 millimeters (mm). The portion of the elongated member to be inserted into and through the accessory channel of the endoscope has an outer diameter of less than 4.2 mm, and preferably has an outer diameter less than or equal to 3.4 mm. A connector 14 on the proximal end of the elongated member enables the member 5 to be quickly connected to and disconnected from the apparatus where the fiber optic member is aligned for receiving infrared radiation from the source. See FIGS. 1, 2, 4A and 4B.

Figure 2:
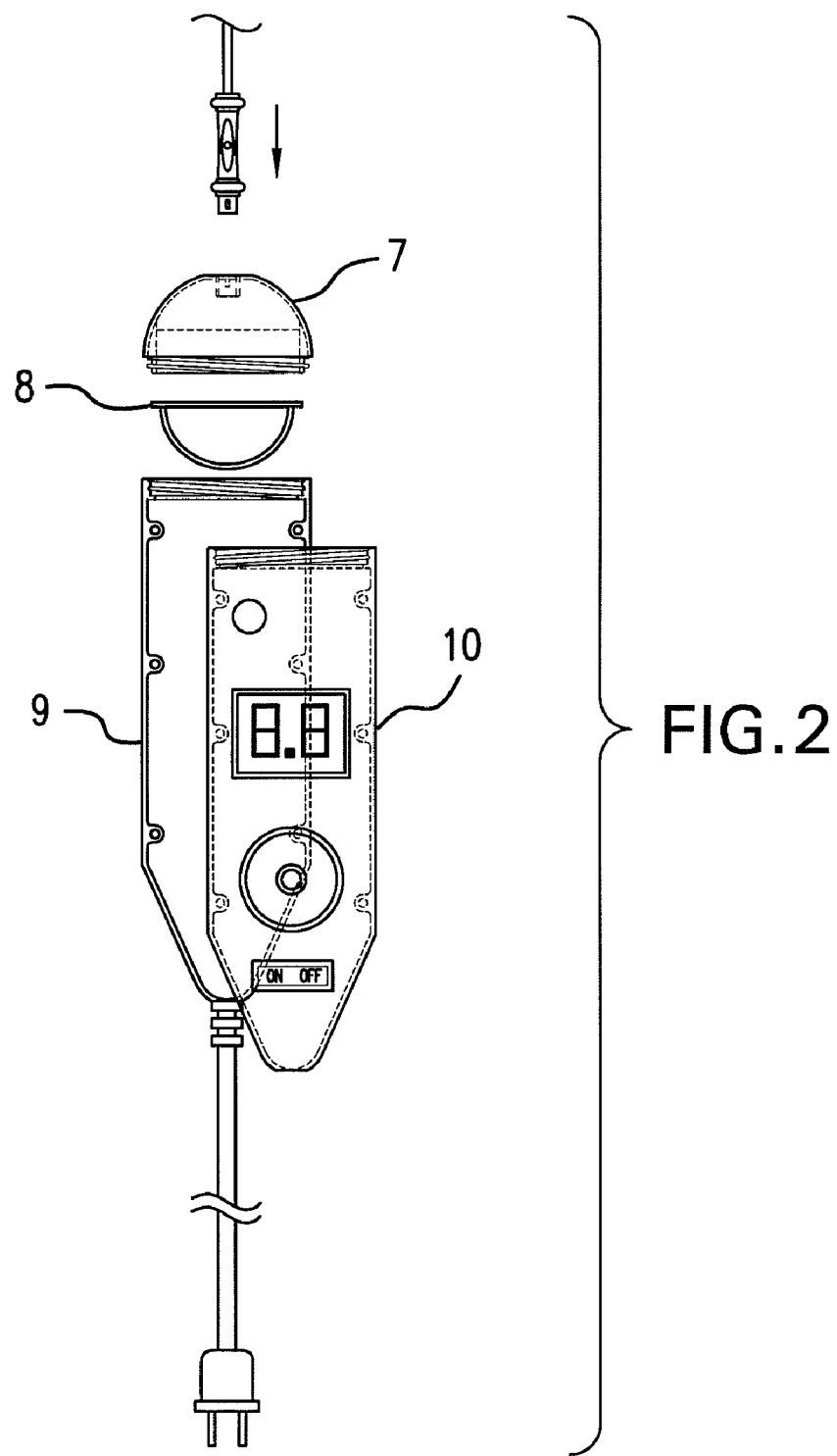
FIG. 2 is top plan view of the control of the apparatus of FIG. 1 shown in disassembled state.
Figure 3:
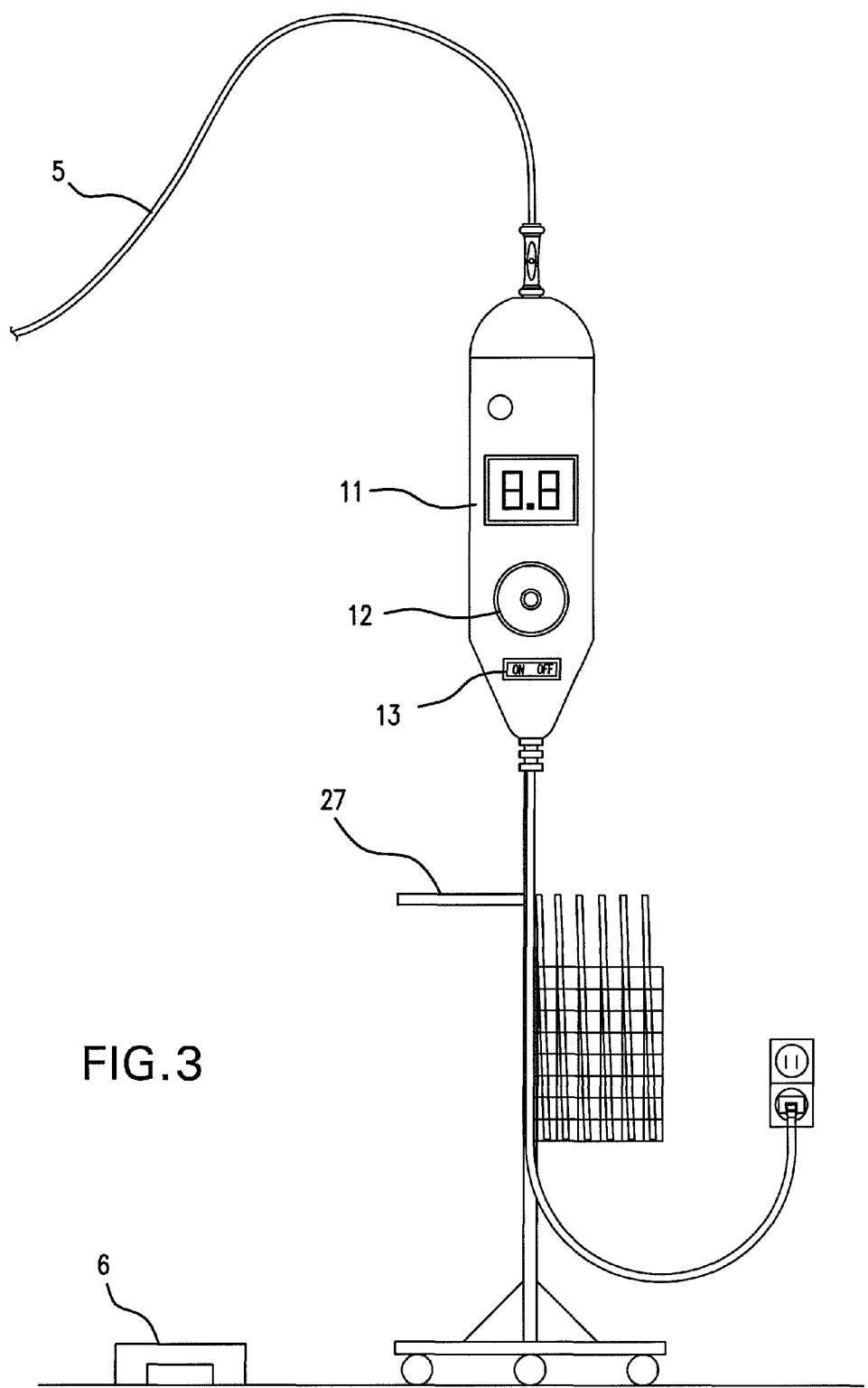
FIG. 3 is a side view of a portion of the apparatus of FIG. 1 mounted on a wheeled cart for use.
Figure 4A:
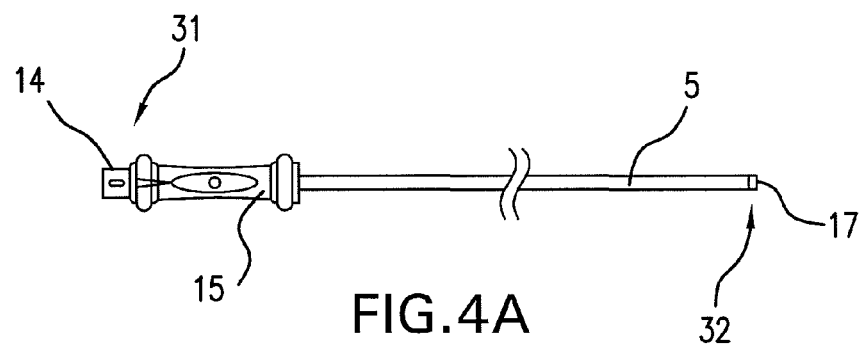
FIG. 4A is a side view of the elongated flexible fiber optic member of the apparatus, sectioned with a middle portion thereof not being shown, depicting the proximal end of the member with a male connector thereon for quick connection to and disconnection from the apparatus, and showing the distal end of the member for engaging human or animal tissue.
Figure 4B:
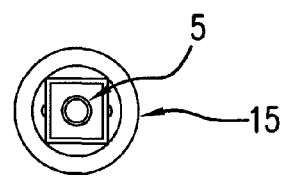
FIG. 4B is an end view of the proximal end of the fiber optic member of FIG. 4A.

The infrared lamp of the source 8 radiates electromagnetic energy primarily in the infrared region but includes both visible and infrared radiation which is transmitted through the elongated flexible fiber optic member 5. A focusing arrangement 7 in the form of a threaded dome-shaped, light-guiding connector mount focuses the radiation from the source onto the proximal end of the fiber optic member. The connector 14 on the proximal end of the member is connected to the light-guiding connector mount 7 by way of an optional activation cord 1 as depicted in FIGS. 1-3. The activation cord 1 extends the length of the flexible fiber optic member. The cord 1 has connectors at each end for optically coupling to the member 5 and control box 3. An optional activator switch may be provided at either of the handles shown near each of the ends of the activating cord 1. The flexible fiber optic bundle of the cord 1 tapers along its length for receiving light and radiation from a larger focused spot at its proximal end and tapering in diameter along its length to deliver radiation to a smaller diameter spot at its distal end where it is optically connected to the member 5. While only a section or portion of the flexible elongated fiber optic member formed by components 5 and 1 in the embodiment is tapered, the member could be tapered over its entire length instead of only along a section or portion thereof.

Figure 6:
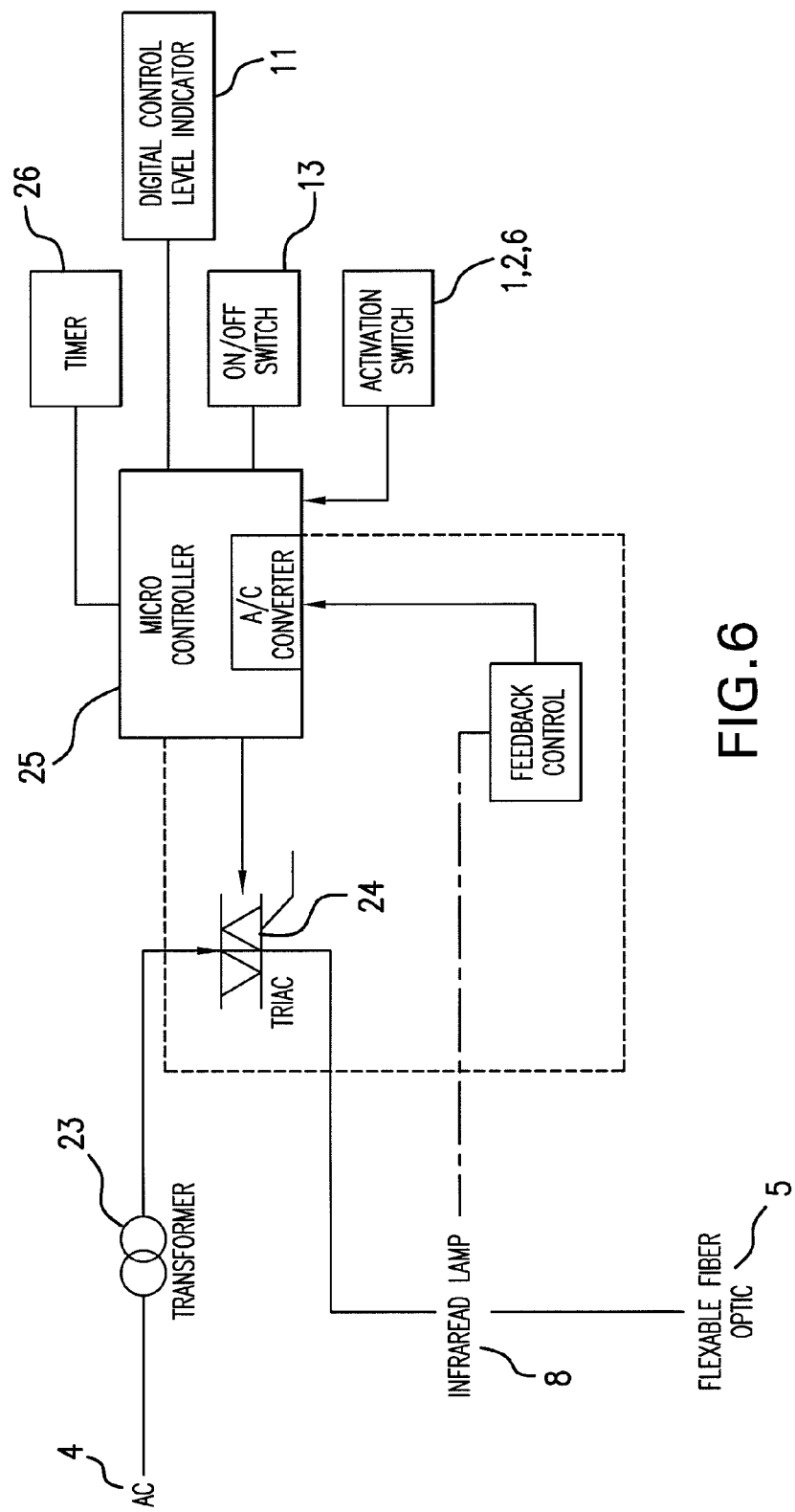
FIG. 6 is an electrical schematic of the control of the apparatus of FIGS. 1-5.

An electrical control 3 of the apparatus 30, in the form of a control box, has an activation switch 2 that when activated provides electrical power to source 8 for producing infrared radiation. An adjustable timer 26 controls the duration of time the source produces radiation after activation of the switch. Activation can also be by way of an optional activation cord 1, or an optional wireless activation switching mechanism 6 depicted in FIG. 1. A power cord 4 provides 110 volt alternating current to the control box wherein the voltage is reduced by a transformer 23 and rectified by a triac 24 under the control of microcontroller 25 to provide a low voltage direct current, such as 15 volts DC, to the infrared lamp 8 as shown in FIG. 6.

The control box 3 of the apparatus 30 is formed with a rear plate 9 with mounting bracket and a front plate 10 as depicted in FIG. 2. The control box has a digital control level display 11 and a control level adjustment knob 12 for the timer 26 which controls the length of time, in seconds, the infrared light source is on after activation as noted above.

Figure 5:
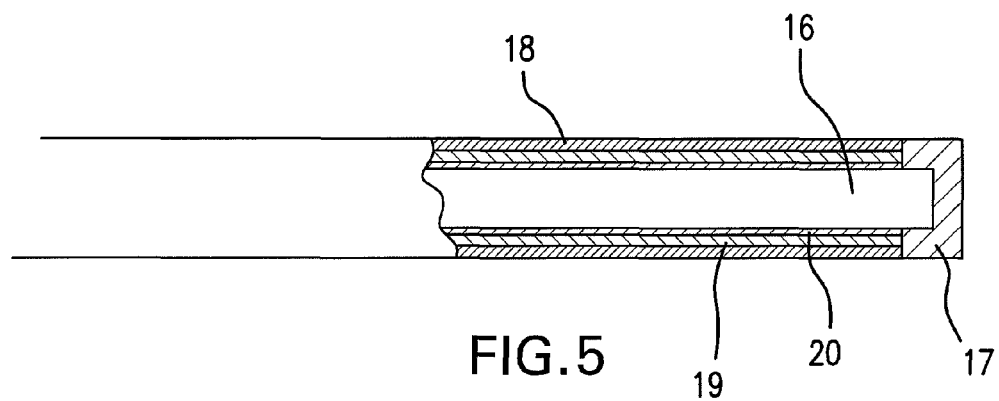
FIG. 5 is an enlarged view of the distal end of the member in FIG. 4, shown partially in cross section along the longitudinal central axis of the member from the distal end, depicting the inner fiber optic body and several outer layers of material thereon as well as a lens or cap on the distal end.

The elongated flexible fiber optic member 5 and optional activation cord 1 each include an inner flexible fiber optic body 16 and an outer protective sheath. As depicted in FIG. 5, the outer protective sheath is formed by a first layer 20 which is a coating or sheath of a highly reflective material such as aluminum. Layer 20 could be aluminum foil, an aluminum tube, or an aluminum coating sprayed on the body 16, for example. A layer 19 of an insulating material such as cellulose or silicone rubber, and a third layer in the form of a single lumen tubing made of plastic or other flexible material are also provided. A lens or cap 17 is attached to the end of the elongated member 5 or formed integral therewith. The lens or cap forms a contact portion at the distal end of the member and controls the size, direction and shape of a radiation delivery area from the member to a material proximate the distal end, e.g. the human or animal tissue when the apparatus is used in a medical application. The lens is preferably formed of a material and construction which minimizes attachment to human or animal tissue during operation of the apparatus since the distal end of the fiber optic members can be placed in contact with the human or animal tissue being treated with the light and infrared radiation from the apparatus. In the example embodiment the elongated flexible fiber optic member preferably has a length within the range of 60 to 230 centimeters depending upon the length of the endoscope to be used with the apparatus.

The apparatus 100 for delivering infrared energy to a material shown in the embodiment of FIGS. 7-14 has a control 118 in the form of a rectangular control box having a back plate 101, a top of enclosure 102, a face plate 103, a bottom of enclosure 104 and a mounting plate 105. A male fiber coupling receptacle 106 is mounted on the face plate 103 for receiving connector 119 of the elongated flexible fiber optic member 117. A tungsten halogen light source 107 providing light and infrared radiation of the type referred to above in connection with the embodiment of FIGS. 1-6 is mounted at critical focal point for transmitting radiation to the fiber optic member 117 connected to the front of the control box.

Figure 9:
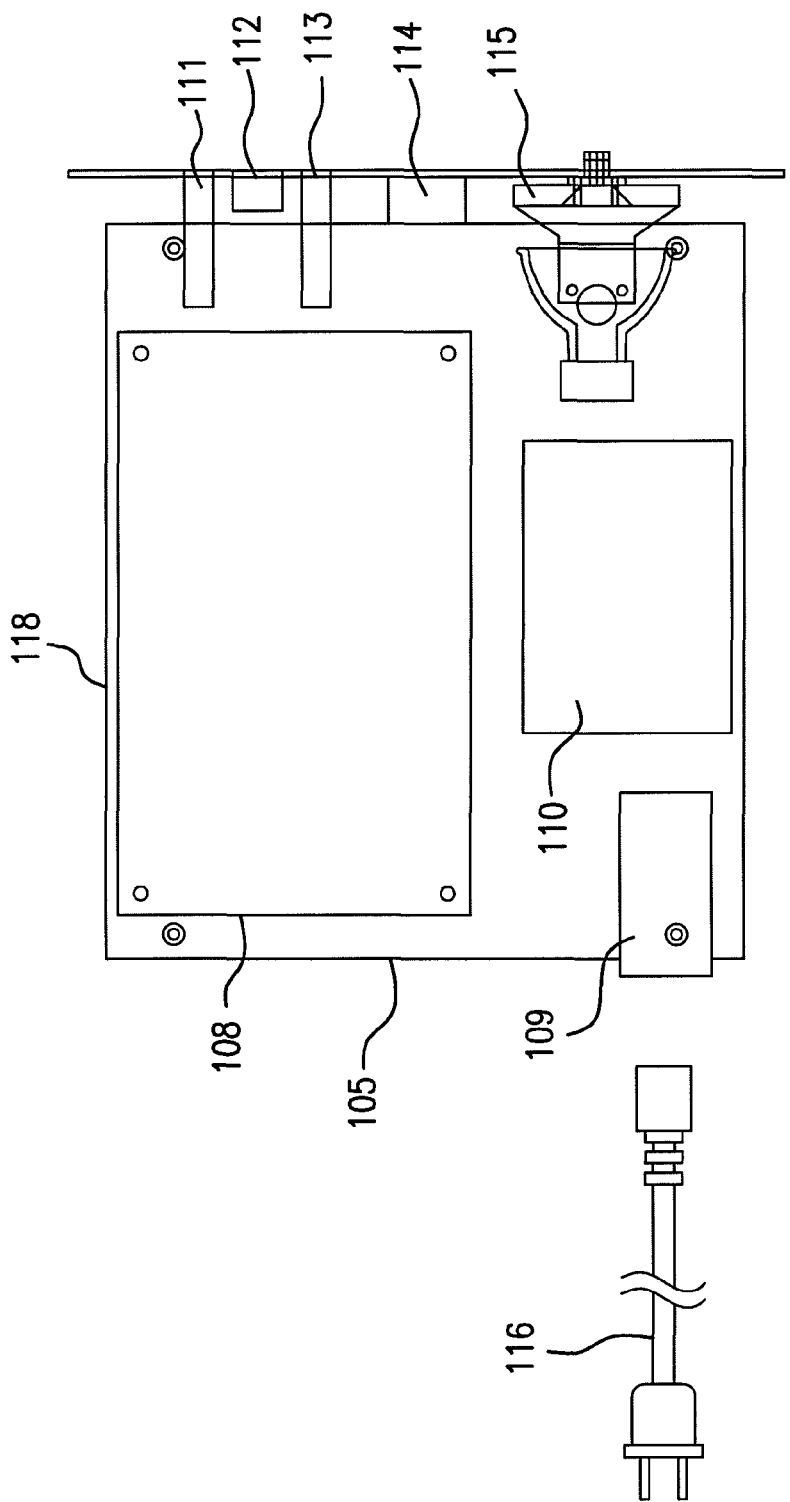
FIG. 9 is a schematic top view of the apparatus of FIG. 7 showing the positional relation of parts of the apparatus with the AC power cord shown unplugged from the apparatus.
Figure 10:
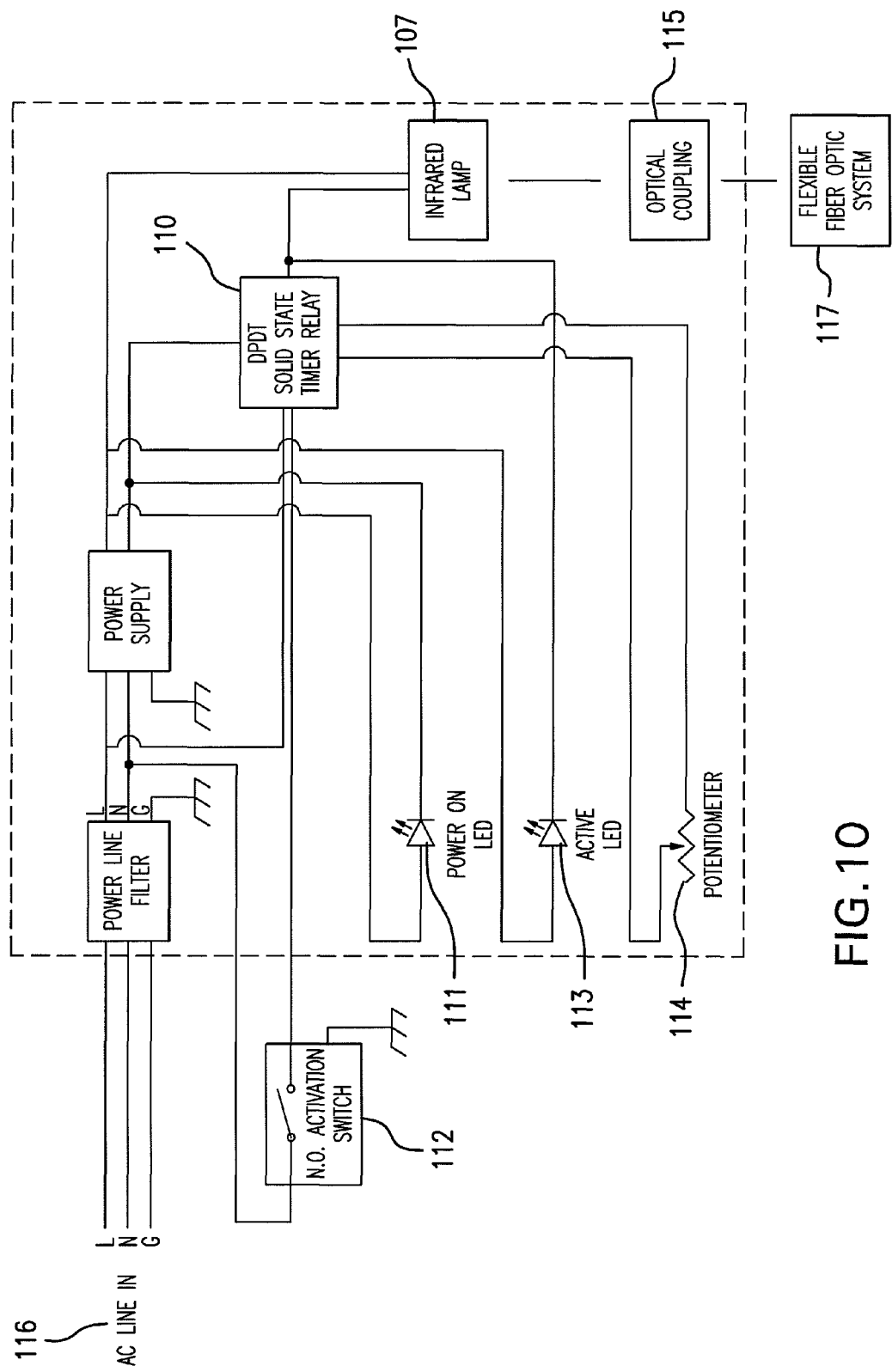
FIG. 10 is an electrical schematic of the control of the apparatus of FIGS. 7-9.

Referring to FIG. 10, the power input to the apparatus is 120 volt alternating current fed into the back of the control box 118 by means of a detachable cord 116. This cord plugs into a power entry module 109 which contains a radio frequency, electromagnetic interference and leakage current filter system. The module also contains an integral switch and dual fuses. The output of the power entry module is 120 volts AC which is fed into two components: the switching power supply 108, FIG. 9, and the activation switch 112. The switching power supply 108 has a working input voltage range of 90 to 264 volts AC and a steady state output of 15 volts DC. It is the main source of power for the infrared light source 107 and also powers the lamp active and power on LEDs 113 and 111, respectively. The activation switch 112 is a normally open switch and when closed, it serves to complete the circuit and provide 120 volt AC to activate the relay which in turn provides power to the infrared light source.

The relay is a solid state timer, designed to control the length of time, in seconds, the contacts are closed and the infrared light source is on. The time range is 0 to 5 seconds. The time is varied by means of a potentiometer 114 connected to an input on the timer relay. The potentiometer is mounted on the front panel of the device and is accessible to the user by means of a rotary knob. The timer relay 110 is a dual pole dual throw (DPDT) type with one contact being used to switch the infrared light source and one contact used to switch the power on LED so they are both activated simultaneously.

When the activation switch is pushed, the timer relay closes, remains closed for the pre-determined length of time, then opens. The timer relay will only stayed closed as long as the activation switch is closed. If it is opened before the pre-determined length of time, the relay contacts will open. The activation switch 112 is operated by a foot operated mechanism 123, see FIG. 7, detachably connected to the control box 118 of the apparatus.

Figure 8:
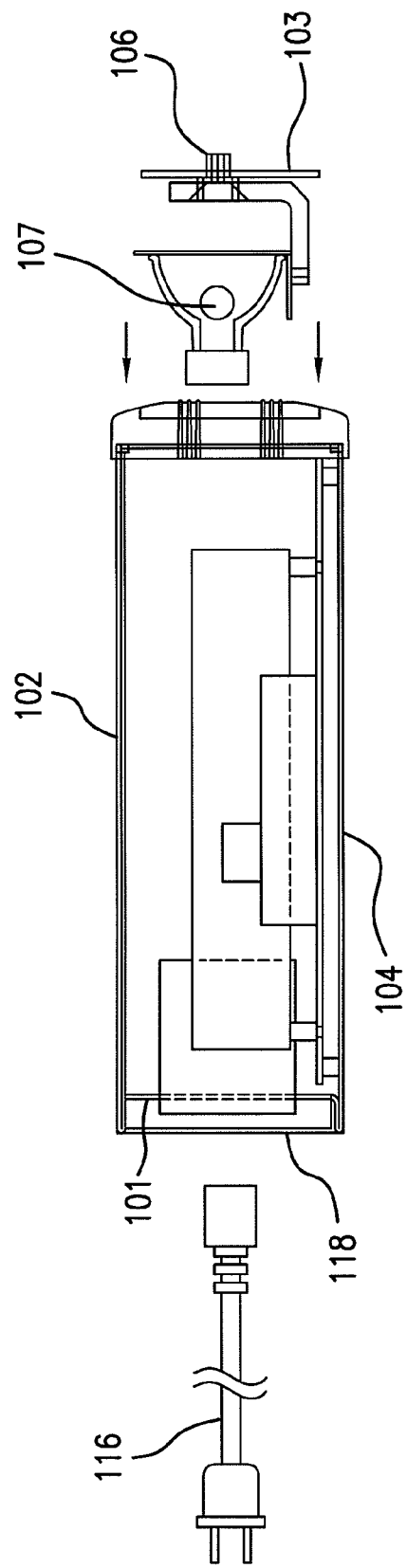
FIG. 8 is a schematic side view of the apparatus of FIG. 7 showing the positional relation of parts of the apparatus with certain parts thereof shown disassembled.

The front panel of the device also contains the threaded receptacle 106 which accepts the connector 119 of the fiber optic bundle of the elongated fiber optic member 117. This receptacle is mounted so that the fiber optic bundle is located in the center of the infrared light source where it is aligned with the infrared radiation from the source. As noted above, the infrared light source is preferably a replaceable 150 Watt tungsten halogen bulb with gold plated reflector, e.g. an ellipsoidal reflector as shown in FIGS. 8 and 9. The light source is mounted in a bracket especially designed so that the reflector's secondary focal point is located precisely at the proximal end of the fiber optic cable when it is mounted in the fiber optic mounting receptacle. When the infrared light source is on, light travels down the fiber optic bundle and exits at the distal end. The entire spectrum of light is transmitted. The optical coupling mount 115 serves as a light guiding connector mount between the infrared radiation source and the elongated flexible fiber optic member connected to the apparatus.

The elongated flexible fiber optic member 117 of the apparatus 100 of FIGS. 7-14 is shown in detail in FIGS. 11 through 14. As seen therein, the flexible fiber optic body 120 of the elongated member 117 is formed of multicomponent glass fiber for near infrared (NIR) wherein the fiber diameter is 55 micrometers and the numerical aperture is 0.57. The diameter of the fiber bundle is 2.8 mm. The length of the flexible fiber optic body is 2.4 meters in the example embodiment. The flexible fiber optic body 120 at its distal end has a metal sleeve 121 with an outer diameter of 3.0 mm adhesively bonded with a high temperature epoxy adhesive about the flexible fiber optic body as depicted in FIGS. 11 and 14. The length of the metal sleeve is 6.35 mm in the example embodiment. The metal sleeve is formed of SUS 304 stainless steel in the example embodiment but other metals could be employed. The connector 119 at the proximal end of the fiber optic body 120 is formed of nickel plated brass and is provided with internal threads for threaded engagement with the male fiber coupling receptacle 106, FIGS. 7, 8 and 11.

The flexible fiber optic body 120 between the connector 119 and the metal sleeve 121 has an outer protective sheath 122 formed by a fluorinated ethylene propylene (FEP) heat shrink tubing, e.g. a compression sheath. The FEP heat shrink tubing is a friction-minimizing material which facilitates insertion of the elongated flexible fiber optic member 117 into and through the accessory channel of an endoscope. Alternatively, the outer protective sheath 122 could be formed of polytetraflouroethylene (PTFE). The outer diameter of the flexible fiber optic body with outer protective sheath is 3.4 mm in the example embodiment but could vary so long as it is less than the internal diameter of the accessory channel in the endoscope it is to be used with. The fiber optic member 117 in the apparatus could also be used in the apparatus 30 of FIGS. 1-6 with any necessary modifications of the connector for optic coupling to the infrared source of the apparatus.

In use, the endoscopic infrared coagulation apparatus of the invention is prepared for use by the physician, nurse, or other attendant by powering on the apparatus as described above and bringing the control box thereof into a position from which it can be reached and viewed as necessary. The control box may be attached to a wheeled cart, 27 in FIG. 3, rack, shelf, or table, or simply placed on a flat surface or held in the hand or worn by the user or one of the attendants.

The elongated flexible fiber optic member of the apparatus is removed from its packaging and attached to the electrical control box, the connector at the proximal end of the fiber optic member being connected to the corresponding fitting associated with the light source within the control box as discussed above. Gripping the elongated fiber optic member between thumb and fingers, the physician inserts the distal tip of the component into the working/accessory channel of the endoscope and pushes the component down the entire length of the endoscope until the distal tip exits the distal end of the endoscope and is visualized on the monitor screen that displays the image generated by the optical system of the endoscope. A contact portion of the distal end of the fiber optic member is placed in physical contact with the tissue to be treated. The timer which controls the duration of the infrared energy pulse from the light source is adjusted based on the physician's judgment of the energy required for coagulation.

Figure 7:
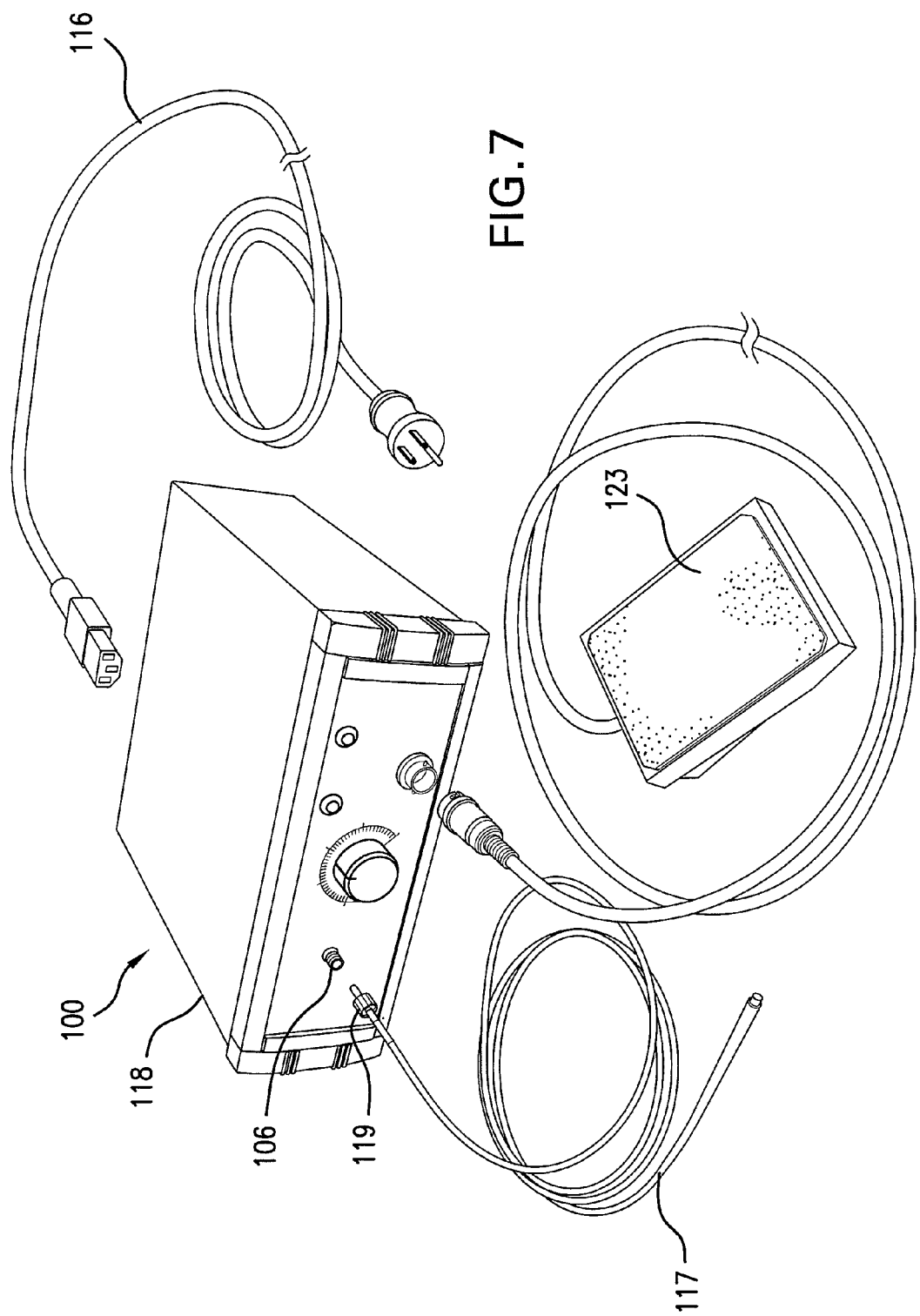
FIG. 7 is a front view of a second, preferred embodiment of an apparatus of the invention for delivering infrared energy to a material, the apparatus components being depicted disconnected from one another.

The apparatus is energized by activating a switch on the control box or the foot switch 123 as shown in FIG. 7. When the activation switch is engaged, electrical power is provided by the control circuit to the infrared radiation source 8, 107 which sends both visible light and infrared energy from the proximal end of the flexible fiber optic member to the distal end. The transfer of infrared energy sent from the contact portion of the distal end to the targeted tissue is such that the temperature of the blood and tissue is raised to the point at which coagulation occurs. The physician visually monitors the treatment site using the optical viewing capabilities of the endoscope and evaluates whether additional coagulation is necessary. If additional treatment is needed the apparatus is activated again and the process is repeated until the physician is satisfied with the results and no further treatment is required. The flexible fiber optic member is removed from the endoscope, disconnected from the control box and disposed in accordance with standard professional practice for the disposal of medical waste.

The metal sleeve 121 exposes a flat polished end of the flexible fiber optic body 120 that is perpendicular to the longitudinal axis of the fiber optic body. This exposed, radiation emitting portion of the fiber optic member provides a contact portion for contacting human or animal tissue or other material being treated with the apparatus. This contact portion defines a size, direction and shape of a radiation delivery area from the member to the tissue or other material proximate the contact portion. In the form of the invention illustrated in FIGS. 7-14, the contact portion defines a radiation delivery area with a direction in only an axial direction with respect to the longitudinal axis of the elongated flexible fiber optic member. However, other possible configurations of the contact portion are illustrated in FIGS. 15A through 19C.

Figure 15A:
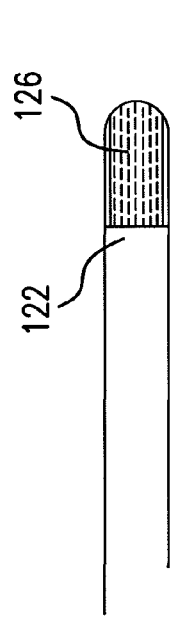
FIG. 15A is a front view showing a contact portion of the distal end of the elongated flexible fiber optic member providing side only energy transfer.
Figure 15B:
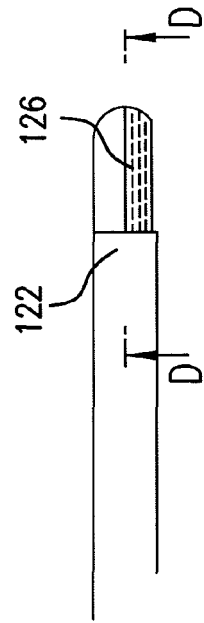
FIG. 15B is a side view of the contact portion of FIG. 15A.
Figure 15C:
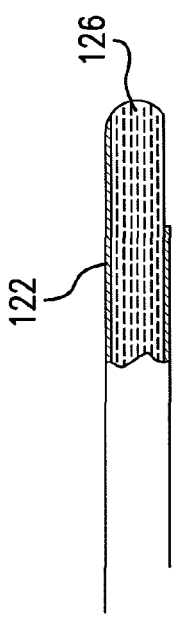
FIG. 15C is a side view cross section taken along the line C-C in FIG. 15B.
Figure 16A:
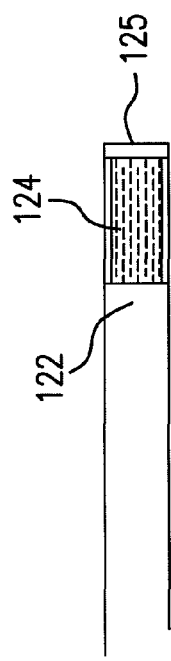
FIG. 16A is a front view showing a radius contact portion with side and end energy transfer.
Figure 16B:
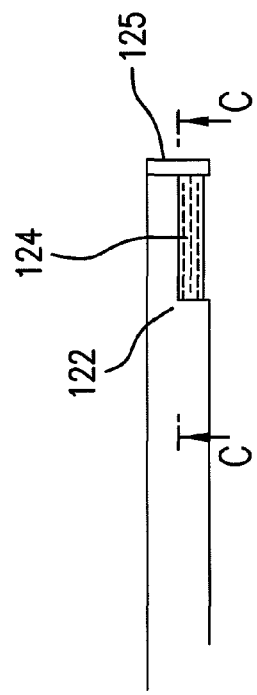
FIG. 16B is a side view of the contact portion of FIG. 16A.
Figure 16C:
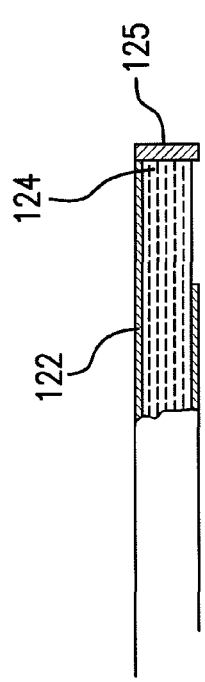
FIG. 16C is a side view cross section taken along the line D-D of the contact portion of FIG. 16B.

The configuration shown in FIGS. 15A-15C permits side-only (transverse) energy transfer. A cut-out 124 in the protective sheath 122 exposes a portion of the fibers, 180° in the example, and a cap or tip 125 is provided which prevents significant infrared radiation transfer longitudinally from the tip. The configuration in FIGS. 16A-16C has a domed or radius tip with the portion of the fibers exposed, 180° or one half of the circumference in the example, along one side of the tip to form the contact portion 126. This allows energy transfer from the end of the fiber optic member, longitudinally, and also from the side, transversely.

Figure 17A:
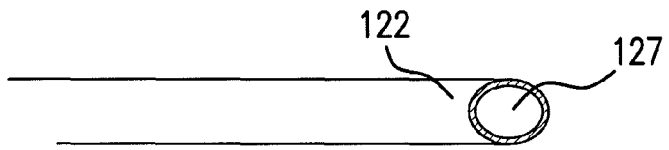
FIG. 17A is a front view of an angle distal contact portion energy transfer arrangement of the distal end of the elongated flexible fiber optic member.
Figure 17B:
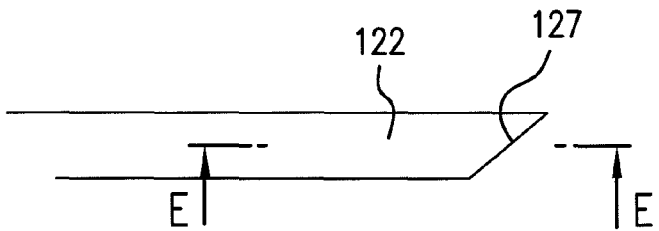
FIG. 17B is a side view of the contact portion of FIG. 17A.
Figure 17C:
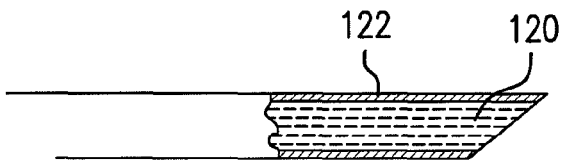
FIG. 17C is a side view cross section taken along the line E-E in FIG. 17B.
Figure 18A:
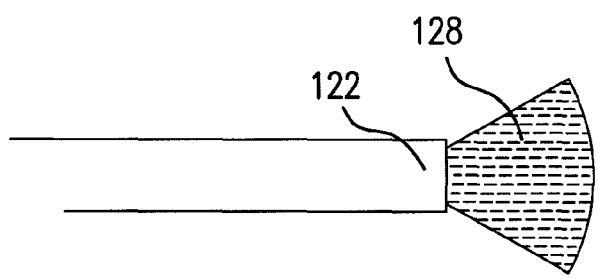
FIG. 18A is a front view of a fan contact portion energy transfer arrangement at the distal end of the elongated flexible fiber optic member.
Figure 18B:
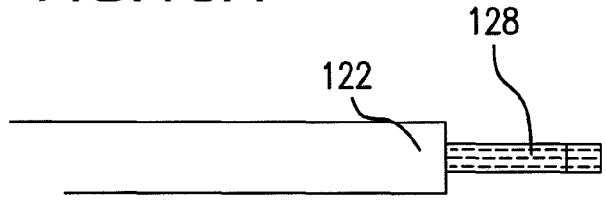
FIG. 18B is a side view of the distal end arrangement of FIG. 18A.

Another configuration of the distal end of the fiber optic member shown in FIGS. 17A-17C includes an angled-tip configuration which provides an elliptical cross-section or contact portion of infrared energy transfer from the tip, rather than the circular cross-section contact portion of the embodiment in FIG. 14. This variation allows transfer of energy to angled surfaces more easily with less articulation of the fiber optic member. A further configuration for the contact portion of the fiber optic member shown in FIGS. 18A and 18B employs a configuration in which the fibers of the flexible fiber optic body are deployed in a fan shape, which allows the apparatus to transfer infrared energy in a delivery area that is much wider than the diameter of the distal end of the flexible fiber optic member itself.

Figure 19A:
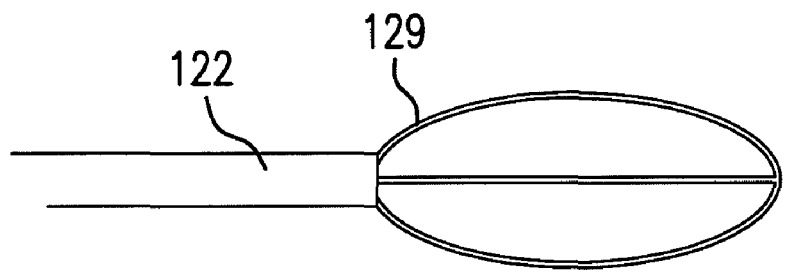
FIG. 19A is a front view of a balloon expanding and/or mechanical expanding contact portion energy transfer arrangement at the distal end of the elongated flexible fiber optic member, only four fibers being shown for explanation purposes.
Figure 19B:
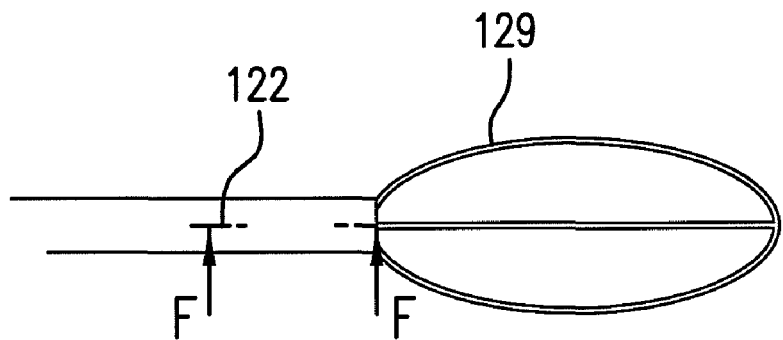
FIG. 19B is a side view of the contact portion arrangement of FIG. 19A.
Figure 19C:
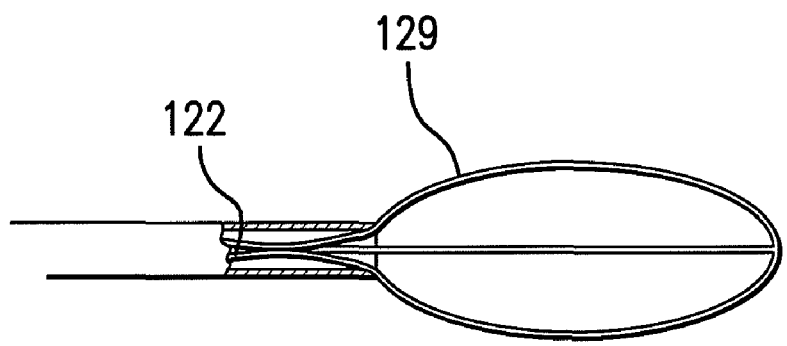
FIG. 19C is a side view cross section taken along the line F-F in FIG. 19B.

A still further configuration of the contact portion, 129 in FIGS. 19A-19C is an arrangement wherein the optical fibers have been expanded by the inflation of a balloon within the fiber bundle or by other mechanical method. In these figures, only four individual fibers are shown, although there may be many fibers arranged in this way. The outer surface of these fibers is broken, such that light and infrared energy exits all along the length of the fibers, allowing energy transfer in all directions around this expanded "bulb" of fibers forming the contact portion 129.

Although the present invention has been described in relation to several embodiments thereof, many other variations and modifications and other uses will become apparent to those skilled in the art. For example, the apparatus of the invention has utility for endoscopy with a borescope in technical situations where direction-of-sight observation and access is not feasible and infrared radiation for treatment of a material is desired. The apparatus of the invention also has utility in such technical situations in which the flexible fiber optic member does not require the use of an endoscope. Various other dimensions and materials of construction for the components of the apparatus could also be used as will be understood by the skilled artisan. The size and heating capability of the apparatus could also be scaled up for large infrared heating applications apart from endoscopy. It is preferred, therefore, that the present invention be limited not by the specific disclosure herein, but only by the appended claims.

We claim:

1. A contact-type, endoscopic infrared coagulation apparatus for delivering infrared energy to human or animal tissue, comprising:
    a source of non-coherent, multiple wavelength, visible and infrared radiation which is not a laser with an ellipsoidal reflector which focuses the radiation at a secondary focal point;
    an elongated, highly flexible fiber optic member which can be used in a retroflexed position, the member having a multicomponent transparent fiber bundle capable of transmitting radiation from the source from a proximal end of the member to a distal end of the member, the distal end having a contact portion defining a radiation delivery area from the member to tissue in contact with the delivery area, an outer compression sheath being provided over the multicomponent transparent fiber bundle;
    a connector on the proximal end of the elongated member for quickly connecting the member to and disconnecting the member from the apparatus where the member is aligned for receiving visible and infrared radiation from the source;
    wherein the elongated member has a length of at least 60 cm and at least the distal end of the elongated member has an outer diameter less than 4.2 mm and the outer compression sheath is formed of a friction-minimizing material enabling removable insertion of the elongated member in a channel of an endoscope until the contact portion of the distal end of the elongated member exits a distal end of the endoscope for contacting tissue to be treated.

2. The apparatus according to claim 1, wherein the source of infrared radiation is an infrared lamp which radiates electromagnetic energy primarily in the infrared region.

3. The apparatus according to claim 1, wherein the reflector focuses the radiation from the source onto the proximal end of the elongated member connected to the apparatus.

4. The apparatus according to claim 3, wherein the elongated member is tapered in diameter over at least a portion of the length of the member for receiving radiation from a larger diameter focused spot from the source, at the proximal end of the member and tapering to said outer diameter of less than 4.2 mm at said distal end to transmit radiation to a smaller diameter spot and for accessing the channel of an endoscope.

5. The apparatus according to claim 1, including a light-guiding connector mount to which the connector on the proximal end of the elongated member can be connected.

6. The apparatus according to claim 1, including an electrical control with a foot activated switch that when activated provides electrical power to the source for producing visible and infrared radiation, and an adjustable timer which controls the duration of time the source produces radiation after activation of the switch.

7. The apparatus according to claim 1, wherein the contact portion defines a size, direction and shape of the radiation delivery area from the member to tissue in contact with the delivery area.

8. The apparatus according to claim 1, wherein the contact portion includes an exposed, radiation emitting portion of the multicomponent transparent fiber bundle of the fiber optic member.

9. The apparatus according to claim 1, wherein the contact portion defines the radiation delivery area with a direction having both radial and axial direction components with respect to a longitudinal axis of the elongated flexible fiber optic member.

10. The apparatus according to claim 1, wherein the contact portion defines the radiation delivery area wider than a diameter of the distal end of the elongated flexible fiber optic member.

11. The apparatus according to claim 1, wherein the contact portion defines the radiation delivery area with a direction in only an axial direction with respect to a longitudinal axis of the elongated flexible fiber optic member.

12. The apparatus according to claim 1, wherein the contact portion is formed of a material and construction which minimizes attachment to the tissue contacted during operation of the apparatus.

13. A contact-type, endoscopic infrared coagulation apparatus for use in a channel of an endoscope to coagulate targeted tissue within a human or animal subject, comprising:
    a source of non-coherent, multiple wavelength, visible and infrared radiation which is not a laser with a reflector which focuses the radiation;
    an elongated, highly flexible fiber optic member which can be used in a retroflexed position, the member having a multicomponent transparent fiber bundle capable of transmitting sufficient infrared radiation from the source from a proximal end of the member to a distal end of the member, the distal end of the member having a contact portion defining a radiation delivery area for contacting human or animal tissue to coagulate targeted tissue, at least the distal end of the elongated member having a diameter less than 4.2 mm and having an outer protective sheath of a friction-minimizing material enabling the distal end of the member to be removably inserted into and through a channel in an endoscope until the contact portion of the distal end of the elongated member exits a distal end of the endoscope for contacting tissue to be treated;
    a connector on the proximal end of the elongated member for quickly connecting the member to and disconnecting the member from the apparatus where the member is aligned for receiving visible and infrared radiation from the source.

14. The apparatus according to claim 13, wherein the friction-minimizing material is selected from the group consisting of polytetrafluoroethylene and fluorinated ethylene propylene.

15. The apparatus according to claim 13, wherein the reflector focuses the radiation from the source onto the proximal end of the elongated member connected to the apparatus.

16. The apparatus according to claim 15, including a light-guiding connector mount to which the connector on the proximal end of the elongated member can be connected.

17. The apparatus according to claim 13, including an electrical control with a foot activated switch that when activated provides electrical power to the source for producing visible and infrared radiation, and an adjustable timer which controls the duration of time the source produces radiation after activation of the activation switch.

18. The apparatus according to claim 13, wherein the contact portion defines a size, direction and shape of the radiation delivery area from the member to human or animal tissue in contact with the delivery area.

19. The apparatus according to claim 13, wherein the contact portion is formed of a material and construction which minimizes attachment to human or animal tissue during operation of the apparatus.

20. The apparatus according to claim 13, wherein the contact portion includes an exposed, radiation emitting portion of the multicomponent transparent fiber bundle of the fiber optic member.

21. The apparatus according to claim 13, wherein the contact portion defines the radiation delivery area with a direction having both radial and axial direction components with respect to a longitudinal axis of the elongated flexible fiber optic member.

22. The apparatus according to claim 13, wherein the contact portion defines the radiation delivery area wider than a diameter of the distal end of the elongated flexible fiber optic member.

23. The apparatus according to claim 13, wherein the contact portion defines the radiation delivery area with a direction in only an axial direction with respect to a longitudinal axis of the elongated flexible fiber optic member.

24. A contact-type method of infrared coagulation using an apparatus comprising a source of non-coherent, multiple wavelength, visible and infrared radiation which is not a laser with a reflector which focuses the radiation;
   an elongated, highly flexible fiber optic member which can be used in a retroflexed position, the member having a multicomponent transparent fiber bundle capable of transmitting sufficient infrared radiation from the source from a proximal end of the member to a distal end of the member, the distal end of the member having a contact portion for contacting human or animal tissue to coagulate targeted tissue, at least the distal end of the elongated member having a diameter less than 4.2 mm and an outer protective sheath of a friction-minimizing material enabling the distal end of the member to be removably inserted into and through a channel in an endoscope until the contact portion of the distal end of the elongated member exits a distal end of the endoscope for contacting tissue to be treated;
   a connector on the proximal end of the elongated member for quickly connecting the member to and disconnecting the member from the apparatus where the member is aligned for receiving visible and infrared radiation from the source; the method comprising:
   connecting the elongated flexible fiber optic member with multicomponent transparent fiber bundle to the source of non-coherent, multiple wavelength, visible and infrared energy,
   inserting the elongated flexible fiber optic member in a channel of an endoscope until the contact portion of the distal end of the member exits a distal end of the endoscope to contact human or animal tissue to be treated, and
   delivering visible and infrared radiation to human or animal tissue in contact with the contact portion of the elongated flexible fiber optic member with the apparatus through the channel of the endoscope.

25. The method of claim 24, including continuing or repeating the delivering to coagulate the human or animal tissue.

* * * * *